United States Patent [19]

Shepard et al.

[11] 4,232,158

[45] Nov. 4, 1980

[54] 10,11-DIHYDRO-5H-DIBENZO[a,d]CY-CLOHEPTEN-5,10-IMINES

[75] Inventors: Kenneth L. Shepard, Ambler, Pa.; Daniel G. Brenner, Medford, Mass.

[73] Assignee: Merck & Co., Inc., Rahway, N.J.

[21] Appl. No.: 45,494

[22] Filed: Jun. 4, 1979

[51] Int. Cl.$^3$ ............................................ C07D 487/08
[52] U.S. Cl. ........................................ 546/72; 424/258; 564/92; 564/184; 564/222; 564/270
[58] Field of Search ........................................ 546/72

[56] References Cited

U.S. PATENT DOCUMENTS

| | | | |
|---|---|---|---|
| 3,542,787 | 11/1970 | Dobson et al. | 546/72 |
| 3,597,433 | 8/1971 | Dobson et al. | 546/72 |
| 3,641,038 | 2/1972 | Davis et al. | 546/72 |
| 3,716,541 | 2/1973 | Dobson et al. | 546/72 |
| 3,717,641 | 2/1973 | Kocsis et al. | 546/72 |
| 3,892,756 | 7/1975 | Nedelec et al. | 546/72 |
| 4,009,273 | 2/1977 | Nedelec et al. | 546/72 |
| 4,052,508 | 10/1977 | Anderson et al. | 546/72 |
| 4,064,139 | 12/1977 | Anderson et al. | 546/72 |
| 4,123,546 | 10/1978 | Haire | 546/72 |

OTHER PUBLICATIONS

March; Advanced Organic Chemistry;McGraw Hill, New York, 1968 pp. 331–332, 689–690.
Villani et al.; J. Het. Chem. vol. 9 pp. 1203–1207 (1972).

*Primary Examiner*—Mary C. Lee
*Attorney, Agent, or Firm*—Mario A. Monaco; William H. Nicholson

[57] ABSTRACT

10,11-Dihydro-5H-dibenzo[a,d]cyclohepten-5,10-imines, derivatives and pharmaceutically acceptable salts thereof are useful as antianxiety agents, as muscle relaxants and in the treatment of extrapyramidal disorders such as in Parkinson's disease. They are prepared by treatment of a 5H-dibenzo[a,d]cyclohepten-5-one with ammonia to give the 5-imine, acylation of the imine, treatment of the protected imine with an organolithium to provide the 5-substituted-5-acylamino compound, treatment with acid or base to cause ring closure to a 5-substituted-5,10-acylimino compound followed by removal of the protecting group, either hydrolytically or hydrogenolytically.

2 Claims, No Drawings

10,11-DIHYDRO-5H-DIBENZO[a,d]CYCLOHEPTEN-5,10-IMINES

BACKGROUND OF THE INVENTION

This invention is concerned with a novel process for the synthesis of 10,11-dihydro-5H-dibenzo[a,d]cyclohepten-5,10-imines which are useful as antianxiety agents, muscle relaxants, and in the treatment of extrapyramidal disorders such as in Parkinson's disease. The products of the novel process have general structural formula:

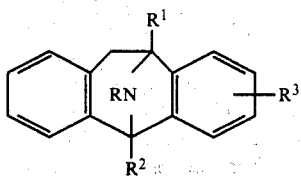

Structurally related compounds are known in the art to have qualitatively similar utilities. For example U.S. Pat. No. 3,892,756 discloses 10,11-dihydro-5H-dibenzo[a,d]cyclohepten-5,10-imine and derivatives, and U.S. Pat. No. 4,064,139 discloses 9,10-dihydro-anthracen-9,10-imines and derivatives. In addition many of the compounds preparable by the novel process of this invention are disclosed in U.S. Patent Application, Ser. No. 912,772.

DETAILED DESCRIPTION OF THE INVENTION

The novel process of this invention is illustrated by the following Reaction Scheme A:

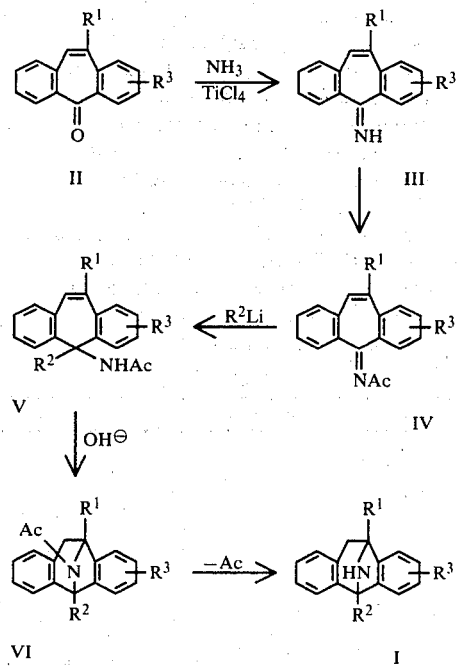

wherein
$R^1$ and $R^2$ are independently,
 (1) $C_{1-5}$ alkyl, preferably methyl or ethyl,
 (2) $C_{2-5}$ alkenyl, preferably vinyl or allyl,
 (3) phenyl-$C_{1-3}$ alkyl, preferably benzyl,
 (4) $C_{3-6}$ cycloalkyl, preferably cyclopropyl or cyclohexyl,
 (5) $C_{3-6}$ cycloalkyl-$C_{1-3}$ alkyl;
or $R^1$ is hydrogen
$R^3$ is hydrogen, or halo; and
Ac is acyl, preferably tosyl, benzenesulfonyl, $C_{1-3}$ alkanoyl, benzoyl, or $C_{1-3}$ alkoxycarbonyl.

The first step in the novel process is formation of the unexpectedly stable imine (III) by treatment of the ketone (II) with gaseous ammonia in the presence of titanium tetrachloride. The reaction is conducted in an inert organic solvent in which the starting materials are soluble, especially an aromatic solvent such as toluene, benzene or the like. The temperature is not critical and may be at about $-10°$ C. to about $+50°$ C. preferably between ice-bath and room temperatures. Times from 2 to about 10 hours are required usually 3 to about 5 hours.

The second step comprises acylating the free imine to form compound IV by treatment of III with an acyl halide such as tosyl chloride, benzenesulfonyl chloride, $C_{1-3}$ lower alkanoyl chloride, benzoyl chloride, or a $C_{1-3}$ lower alkyl chloroformate. Standard acylating conditions are employed such as contacting the two reagents in an inert organic solvent in the presence of an acid acceptor such as an organic base, especially pyridine which can also be used as the solvent, triethylamine, or an inorganic base, especially an alkali metal carbonate, or an alkaline resin, or the like. Reaction times and temperatures of 1 to 6 hours at about 0° C. to about 50° C. especially 2 to 4 hours at ice bath temperature to room temperature are employed, although prolonged reaction times are not detrimental.

The third step comprises the addition of $R^2H$ across the imine double bond. Compound IV is treated with an organolithium in an inert organic solvent, especially an ether such as diethyl ether, tetrahydrofuran, 1,2-dimethoxyethane or the like at 0° C. to about 50° C., preferably room temperature for 0.5-4 hours, preferably about 1-3 hours. Prolonged stirring times are not detrimental.

The fourth step results in formation of the imine bridge by addition of the acylamine group across the conjugated double bond. The cyclization may be effected by treatment with a base such as an alkali metal hydroxide, especially sodium or potassium hydroxide in a high boiling ethereal type solvent such as diglyme. Reaction temperatures and times of about 150° to about 170° C. for about 24 to about 48 hours are employed.

The fifth and last step, formation of compound I, comprises deacylation of the imine group. These acyl groups are conveniently removed by acid or base hydrolysis at 25° to about 150° C. for 2 to 48 hours, preferably 6 to about 24 hours. Strong mineral acids such as hydrochloric, sulfuric or the like are employed and may be admixed with organic acids such as acetic or the like. In the case of the arylsulfonyl protective groups they are also removed by hydrogenolysis with an excess of sodium bis(2-methoxyethoxy)aluminum hydride in an inert organic solvent such as toluene at about 15° C. to about 50° C., preferably at 20° C. to about 30° C. for 6-48 hours, preferably about 12-24 hours.

The compounds preparable by the novel process of this invention are capable of producing anxiety relief without causing excessive sedation or sleep at a dosage level of from about 0.01 to about 50 mg per kilogram of body weight preferably about 0.5-10 mg/kg of body weight on a regimen of 1-4 times a day. In addition, they are useful as muscle relaxants, anticonvulsants and in the treatment of extrapyramidal disorders when indicated at comparable dosage levels. The exact treatment level will depend upon the case history of the animal or human individual being treated and in the last analysis the precise treatment level falling within the above guidelines is left to the discretion of the therapist.

Pharmaceutical compositions comprising the imines prepared by the novel process of this invention are preferably in unit dosage forms such as tablets, pills, capsules, powders, granules, sterile parenteral solutions or suspensions, or suppositories for oral, parenteral or rectal administration.

EXAMPLE 1

5-Methyl-10,11-Dihydro-5H-Dibenzo[a,d]cyclohepten-5,10-Imine

Step A: Preparation of 5H-dibenzo[a,d]cyclohepten-5-imine

Ammonia gas is bubbled slowly over a thirty minute period into an ice-cooled, stirred mixture of 25 g of 5H-dibenzo[a,d]cyclohepten-5-one and 10 ml of titanium tetrachloride in 750 ml of toluene. The cooling bath is removed and stirring is continued while the mixture warms to room temperature. The mixture is then refluxed 5½ hours. The mixture is added to one liter of saturated aqueous sodium carbonate solution with stirring. The toluene layer is washed with 500 ml of saturated sodium carbonate solution and 300 ml of saturated sodium chloride solution. The original aqueous layer is extracted with 2×500 ml of ethylacetate and the combined extracts are washed with saturated sodium carbonate and sodium chloride. The toluene phase and ethyl acetate extracts are combined and dried over anhydrous sodium sulfate and concentrated to dryness. The residue on trituration with petroleum ether gave 20.6 g of 5H-dibenzo[a,d]cyclohepten-5-imine, m.p. 60°-62° C.

Step B: Preparation of 5-p-toluenesulfonimino-5H-dibenzo[a,d]cycloheptene p-Toluenesulfonyl chloride (22.3 g) is added portionwise to an ice-cooled, stirred solution of 24 g of 5H-dibenzo[a,d]cyclohepten-5-imine in 300 ml of pyridine. The ice-bath is removed and stirring is continued at room temperature (~20° C.) over the weekend. Methylene chloride (600 ml) is added and the mixture is extracted with 3×500 ml of 1N hydrochloric acid. The methylene chloride phase is dried over anhydrous sodium sulfate and concentrated to dryness. The residue (39.2 g) is recrystallized by dissolving in 800 ml of hot ethanol, filtering, concentrating to 500 ml and cooling to give 16.7 g 5-p-toluenesulfonimino-5H-dibenzo[a,d]cycloheptene, which on recrystallization from ethanol has m.p. 156.5°-158.5° C.

Step C: Preparation of 5-methyl-5-p-toluensulfonamido-5H-dibenzo[a,d]cycloheptene A solution of 5.0 g of 5-p-toluenesulfonimino-5H-dibenzo[a,d]cyclohpetene in 75 ml of dry tetrahydrofuran is stirred under nitrogen and treated dropwise with 30 ml of 1.4M methyllithium in ether. After stirring overnight at room temperature under nitrogen, the reaction mixture is added to 100 ml of 10% (w/v) aqueous ammonium chloride. The mixture is extracted with ethyl acetate. The extract is washed with water and saturated sodium chloride solution, filtered, dried over anhydrous sodium sulfate and concentrated to dryness to give 6.4 g of product which after recrystallization from ethanol gives 2.8 g of 5-methyl-5-p-toluensulfonamido-5H-dibenzo[a,d]cycloheptene, m.p. 175°-178° C.

Step D: Preparation of 5-methyl-12-p-toluenesulfonyl-5H-dibenzo[a,d]cyclohepten-5,10-imine A mixture of 1 g of 5-methyl-5-p-toluenesulfonamido-5H-dibenzo[a,d]cycloheptene and 5 g of potassium hydroxide pellets (86.1%) in 50 ml of diglyme is heated in an oil bath at 160°-170° C. for 42 hours. The mixture is added to 200 ml of water and neutralized (pH 7) with concentrated hydrochloric acid. The solution is extracted with 2×200 ml of ether and each of the ether extracts are back washed with 3×100 ml of water. The ether extracts are separately dried over anhydrous sodium sulfate, filtered and concentrated to dryness to give 330 mg and 100 mg respectively of product. Recrystallization from ethanol and drying provides 5-methyl-12-p-toluenesulfonyl-5H-dibenzo[a,d]cyclohepten-5,10-imine, m.p. 186.5°-188.5° C.

Step E: Preparation of 5-methyl-10,11-dihydro-5H-dibenzo[a,d]cyclohepten-5,10-imine A mixture of 290 mg of 5-methyl-12-p-toluenesulfonyl-5H-dibenzo[a,d]cyclohepten-5,10-imine, 5 ml of concentrated hydrochloric acid, and 5 ml of glacial acetic acid is refluxed overnight. The clear solution is added to 100 ml of water and 20% (w/v) aqueous sodium hydroxide is added to pH 9. The mixture is extracted with 3×100 ml of methylene chloride. The extract is washed with saturated aqueous sodium chloride solution, dried over anhydrous sodium sulfate and evaporated to give 210 mg of oil. The oil is dissolved in acetone and treated with 142 mg of oxalic acid in acetone. The mixture is cooled and the precipitate is collected to give 100 mg 5-methyl-10,11-dihydro-5H-dibenzo[a,d]cyclohepten-5,10-imine, m.p. 211°-212° C.

Following the procedure substantially as described in Example 1, but substituting for the 5H-dibenzo[a,d]cyclohepten-5-one used in Step A, and the methyllithium used in Step C, the $R^1$-$R^3$-5H-dibenzo[a,d]cyclohepten-5-ones and the organolithiums of formula $R^2Li$ described in Table I there are produced the $R^1$-$R^2$-$R^3$-10,11-dihydro-5H-dibenzo-[a,d]cyclohepten-5,10-imine also described in Table I in accordance with the processes of Reaction Scheme A.

TABLE I

| $R^1$ | $R^3$ | $R^2$ |
|---|---|---|
| CH₃— | 3-Br | CH₃— |
| n-C₃H₇ | 2-Br | n-C₃H₇ |
| CH₂=CH—CH₂— | H | 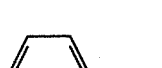 |
|  | H | C₂H₅— |
|  | 6-Br | CH₂=CHCH₂— |
|  | H |  |

TABLE I-continued

| R¹ | R³ | R² |
|---|---|---|
| | 7-Br | |
| cyclohexyl-CH₂— | | cyclohexyl |
| cyclopropyl-CH₂— | H | CH₃— |
| C₂H₅— | 2-F | CH₃— |
| CH₃— | 3-F | cyclopropyl-CH₂— |
| H | 3-Br | CH₃— |
| H | 7-Br | CH₃— |
| H | 3-F | CH₃— |

EXAMPLE 2

Tablet Preparation

Tablets containing 1.0, 2.0, 25.0, 26.0, 50.0, and 100.0 mg, respectively, of 10,11-dihydro-5-methyl-5H-dibenzo[a,d]cyclohepten-5,10-imine are prepared as illustrated below.

| TABLE FOR DOSES CONTAINING FROM 1-25 MG OF THE ACTIVE COMPOUND | | | |
|---|---|---|---|
| | Amount - mg | | |
| 10,11-dihydro-5-methyl-5H-dibenzo[a,d]cyclohepten-5,10-imine | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount - mg | | |
| 10,11-dihydro-5-methyl-5H-dibenzo[a,d]cyclohepten-5,10-imine | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet.

What is claimed is:

1. A process for the preparation of a compound of structural formula:

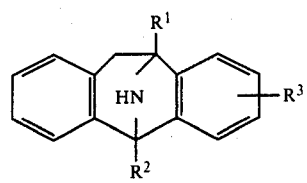

wherein
R¹ and R² are independently (1) $C_{1-5}$ alkyl,
(2) $C_{2-5}$ alkenyl,
(3) phenyl-$C_{1-3}$ alkyl,
(4) $C_{3-6}$ cycloalkyl, or
(5) $C_{3-6}$ cycloalkyl-$C_{1-3}$ alkyl; or R¹ is hydrogen R³ is (1) hydrogen, or
(2) halogen;

which comprises the following steps, in sequence:

(a) treatment of a compound of formula:

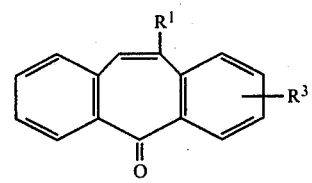

with gaseous ammonia in the presence of titanium tetrachloride;

(b) treatment of the resulting imine of structure:

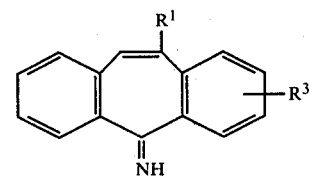

with an acylating agent selected from tosyl chloride, benzenesulfonyl chloride, $C_{1-3}$ alkanoyl chloride, benzoyl chloride and a $C_{1-3}$ lower alkyl chloroformate in the presence of an acid acceptor;

(c) treatment of the resulting acylimine of structure:

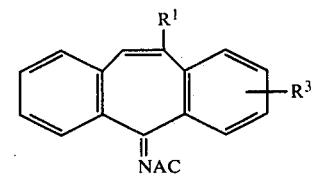

wherein Ac is, tosyl, benzenesulfonyl, $C_{1-3}$ alkanoyl, benzoyl, or $C_{1-3}$ alkoxycarbonyl with an organolithium of formula $R^2Li$;

(d) treatment of the resulting acylamide of structure:

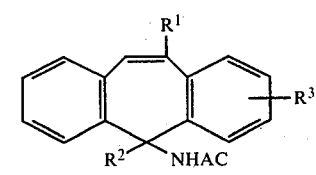

with an alkali metal hydroxide to produce the acylimine of structure:

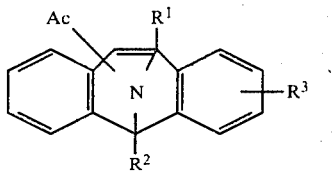
(e) treatment of the acylimine of Step (d) with a strong acid or strong base, or where Ac is an arylsulfonyl group with a strong acid or, sodium bis(2-methoxyethoxy)aluminum hydride to produce the imine of formula:
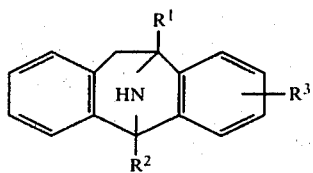
2. The process of claim 1 for the preparation of the compound wherein $R^1$ is hydrogen, $R^2$ is methyl, and $R^3$ is hydrogen.
* * * * *